United States Patent [19]

Weeks

[11] Plant 4,712

[45] May 12, 1981

[54] ROSE PLANT

[76] Inventor: O. L. Weeks, 4759 Philadelphia St., Chino, Calif. 91710

[21] Appl. No.: 142,405

[22] Filed: Apr. 21, 1980

[51] Int. Cl.[3] ..... A01H 5/00

[52] U.S. Cl. ..... Plt./11

[58] Field of Search ..... Plt./11, 18

*Primary Examiner*—Robert E. Bagwill

*Attorney, Agent, or Firm*—Vincent G. Gioia

[57] ABSTRACT

A new hybrid tea rose variety of peach flower coloring, and handsome, large leafed plant with attractive foliage.

1 Drawing Figure

1

The present invention relates to a new and distinct variety of rose plant of the hybrid tea rose class, which was originated by my crossing as seed parent the rose known as "Arizona" and an unnamed, unpatented and unreleased rose seedling of my creation as pollen parent.

Among the novel characteristics possessed by this new variety which distinguish it from its parents and all other varieties of which I am aware are peach, substantially non-fading, symmetrical, singly borne blooms, and a vigorous, free branching plant with abundant large attractive dark green foliage. Asexual reproduction by budding of the new variety as performed in San Bernardino County, Calif., shows that the foregoing and other distinguishing characteristics come true to form and are established and transmitted through succeeding propagations.

The new and improved rose variety which I have developed is an unusually fine hybrid tea rose with singly-borne, heavily petaled blooms of symmetrical, hybrid-tea form displayed on a vigorous upright, free branching plant with abundant large leafed, dark green foliage such that the plant is most attractive between blooming periods. The peach coloring of the blooms holds well and open blooms are also attractive.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with the Royal Horticultural Society Color Chart (RHSCC). The terminology used in color description herein refers to plate numbers in the aforementioned color chart, e.g., "27C" is plate 27C of the Royal Horticultural Society Color Chart.

Parentage: Seedling.

*Seed parent.*—"Arizona".

*Pollen parent.*—Unnamed, unreleased seedling of my creation.

Class: Hybrid tea.

The following observations are made of specimens grown outdoors in San Bernardino County, Calif. during the month of October.

1. FLOWER

Blooming habit: Intermittent to continuous.

A. Bud:

2

(1) *Size.*—Medium.

(2) *Form.*—Short, pointed.

(3) *Color.*—When sepals first divide bud is mixture of greenish yellow (at petal point of attachment), pale yellow and reddish tones.

(4) *Sepals.*—Simple, about same length as bud or slightly longer, foliated.

(5) *Peduncle.*—Length — medium, prickly. Aspect — straight. Strength — erect. Color — reddish green.

B. Bloom:

(1) *Size.*—Average size when fully expanded — about 4 to 4½-inches.

(2) *Borne.*—Primarily singly.

(3) *Form.*—Globular, opening with circular outline, overlapping petals give ruffle effect.

(4) *Petalage.*—Number of petals under normal conditions — about 50.

(5) *Color.*—As petals unfurl lighter petal undersurface 27C is seen. As flower opens further darker top petal surface 179D becomes more noticeable. Overall color effect of partially opened bloom is peach 29C. As flower matures some pink edging is additionally seen but outer petals lighten to 29D.

C. Petals:

(1) *Texture.*—Medium thick.

(2) *Appearance.*—Velvety to satiny.

(3) *Form.*—Obovate.

(4) *Arrangement.*—Regularly arranged.

(5) *Petaloids in center.*—Few.

(6) *Persistence.*—Drop off cleanly.

(7) *Fragrance.*—Slight.

(8) *Lasting quality.*—Long lasting on plant and as cut flower.

2. REPRODUCTIVE ORGANS

A. Stamens, Filaments and anthers:

(1) *Arrangement.*—Many stamens about pistils, short filaments.

(2) *Color.*—Yellow.

B. Pollen: Color — yellow.

C. Styles: Uneven, medium length, bunched.

D. Stigmas: Color — yellow.

E. Hips: None observed.

3. PLANT

A. Form: Upright, tall.

B. Growth: Vigorous, free branching.

C. Foliage: Compound 3 to 5 leaflets.

(1) *Size.*—Large.

(2) *Quantity.*—Abundant.

(3) *Color.*—New foliage: reddish green. Old foliage: Upper side — 139A. Under side — 139C.

(4) *Shape.*—Ovoid, emarginate.

(5) *Texture.*—Upper side is glossy and under side is dull.

(6) *Edge.*—Serrated.

(7) *Serration.*—Simple.

(8) *Leaf stem.*—Color — near to 139A. Under side — 139C.

(9) *Stipules.*—Medium.

(10) *Resistance to disease.*—Mildew — good. Rust — good.

D. Wood:

(1) *New wood.*—Color — near 148B. Bark — smooth, shiny.

(2) *Old wood.*—Color — near 147A. Bark — smooth, shiny.

E. Thorns:

(1) *Thorns.*—Quantity (main stalk): ordinary. On laterals from stalk — ordinary. Form — straight. Length — medium. Color — light green to tan. Position — scattered.

(2) *Prickles.*—Many.

F. Winter hardiness: Good winter hardiness.

I claim:

1. A new and distinct variety of rose plant of the hybrid tea class, substantially as shown and described, characterized particularly by peach colored flowers of heavy petalage borne primarily singly to a stem and a vigorous plant with abundant attractive dark green foliage.

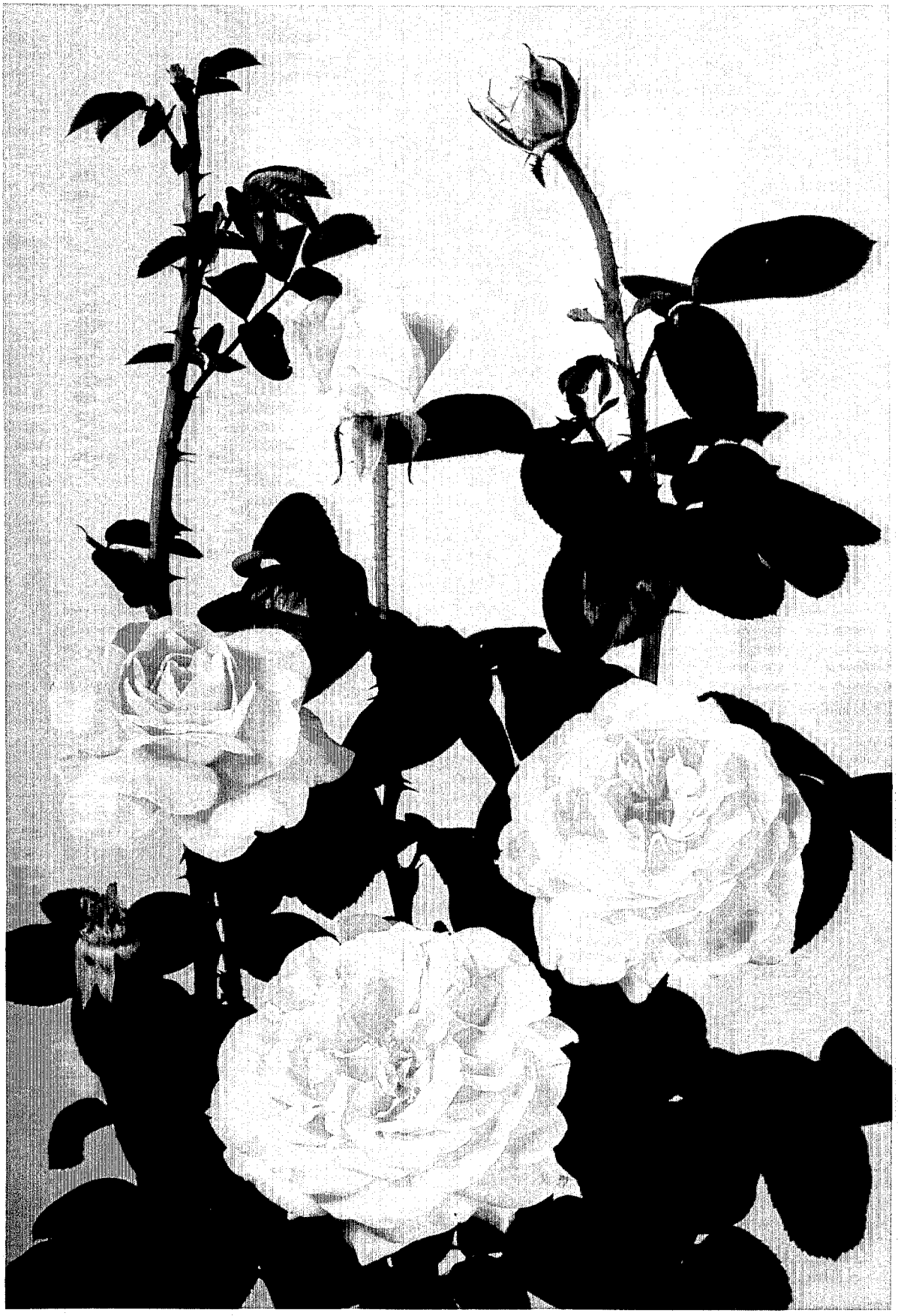

* * * * *